(12) United States Patent
Hoefle et al.

(10) Patent No.: US 6,197,802 B1
(45) Date of Patent: Mar. 6, 2001

(54) FUNGICIDAL MELITHIAZOLE DERIVATIVES

(75) Inventors: Gerhard Hoefle; Udo Soeker, both of Braunschweig; Annerose Rehnig, Ingelheim; Gerhard Ewald Sieverding, St. Johann, all of (DE)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/402,855

(22) PCT Filed: Apr. 8, 1998

(86) PCT No.: PCT/US98/06935

§ 371 Date: Jan. 19, 2000

§ 102(e) Date: Jan. 19, 2000

(87) PCT Pub. No.: WO98/46583

PCT Pub. Date: Oct. 22, 1998

(30) Foreign Application Priority Data

Apr. 11, 1997 (DE) ................................. 197 15 290
Jan. 27, 1998 (EP) .................................. 98101365

(51) Int. Cl.$^7$ .......................... C07D 277/30; A01N 43/78
(52) U.S. Cl. ........................... 514/365; 548/200; 548/204
(58) Field of Search .................... 548/200, 204; 514/365

(56) References Cited

PUBLICATIONS

Bohlendorf Eur J Org Chem 1999 (10) 2601–8, Oct. 1999.*

* cited by examiner

*Primary Examiner*—Robert Gerstl
(74) *Attorney, Agent, or Firm*—Barbara L. Renda; Barbara V. Maurer

(57) ABSTRACT

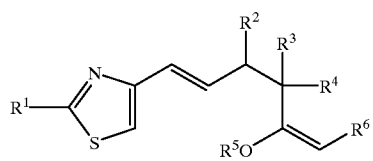

Compounds of formula (I), wherein $R^1$ represents a hydrogen atom or an optionally substituted alkyl, alkenyl, alkyloxiranyl, alkanoyl, alkoxycarbonyl, formyl, hydroxyalkyl, alkoxyalkyl, alkanoyloxyalkyl, hydroxyiminoalkyl, alkoxyiminoalkyl, hydrazonoalkyl or alkylhydrazonoalkyl group; $R^2$ represents an alkoxy group; $R^3$ and $R^4$ each independently represent a hydrogen atom or an alkyl group; $R^5$ represents an alkyl group, and $R^6$ represents a group of formula —$COOR^7$ or —$CONR^7R^8$, in which $R^7$ and $R^8$ show excellent fungicifal activity and systemicity and are thus useful in various agricultural applications.

16 Claims, No Drawings

FUNGICIDAL MELITHIAZOLE DERIVATIVES

BACKGROUND OF THE INVENTION

This invention relates to novel melithiazole derivatives, a process for their preparation, compositions containing such compounds, a method for combating a fungus at a locus comprising treating the locus with such compounds and their use as fungicides.

Food production relies upon a variety of agricultural technologies to ensure the growing population's dietary needs remain affordable, nutritious and readily available on grocery store shelves. Fungicides are one of these agricultural technologies which are available to the world community. Fungicides are agrochemical compounds which protect crops and foods from fungus and fungal diseases. Crops and food are constantly threatened by a variety of fungal organisms, which, if left uncontrolled, can cause ruined crops and devastated harvests.

The preparation of melithiazole C by reductive cleavage of myxothiazol A with subsequent transformation of the resulting melithiazole C amide into the corresponding methyl ester has been described by a poster of B. Böhlendorf et al. presented at the Dechema Naturstofftagung in Irsee, Germany in 1996. Melithiazole C disclosed on this poster shows weak in vitro activity against *Bortrytis cinera*.

There is no indication that this compound could be active in vivo against other phytopathogenic fungi. Moreover, there is no hint to other derivatives of melithiazole C.

The underlying problem of the present invention was to find novel melithiazole derivatives having high in vivo activity against a broad range of phytopathogenic fungi.

SUMMARY OF THE INVENTION

The present invention provides novel melithiazole derivatives of the general formula I

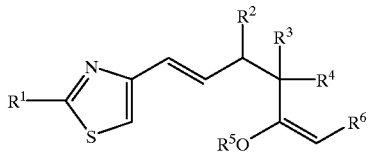

(I)

wherein $R^1$ represents a hydrogen atom or an optionally substituted alkyl, alkenyl, alkyloxiranyl, alkanoyl, alkoxycarbonyl, formyl, hydroxyalkyl, alkoxyalkyl, alkanoyloxyalkyl, hydroximinoalkyl, alkoxyiminoalkyl, hydrazonoalkyl or alkylhydrazonoalkyl group;

$R^2$ represents an alkoxy group;

$R^3$ and $R^4$ each independently represent a hydrogen atom or an alkyl group;

$R^5$ represents an alkyl group, and $R^6$ represents a group of formula —COOR$^7$ or —CONR$^7$R$^8$, in which R$^7$ and $R^8$ each independently represent a hydrogen atom or an alkyl group; with the proviso that melithiazole C or the corresponding amide of formula,

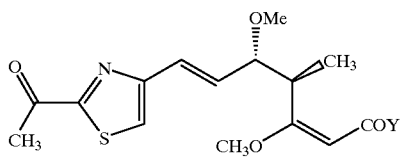

wherein Y represents NH$_2$ or OCH$_3$, are excluded.

The new compounds combine excellent fungicidal activities against a broad range of phytopathogenic fungi in various crops with comparably high systemicities.

It is also an object of the invention to provide methods for controlling an undesired fungus by contacting said plants with a fungicidally effective amount of the new compounds.

It is another object of the invention to provide fungicidal compositions containing the new compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that melithiazole derivatives of the general formula I

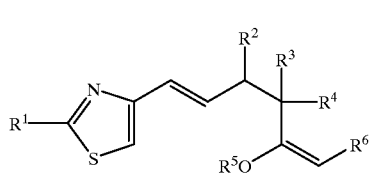

(I)

wherein $R^1$ through $R^6$ are as hereinbefore defined, and excluding melithiazole C or the corresponding amide thereof, combine excellent fungicidal activity against diseases caused by phytopathogenic fungi even at low dose rates with high bioavailability due to their high systemicity.

Optionally substituted moieties may be unsubstituted or have from one up to the maximal possible number of substituents. Typically, 0 to 2 substituents are present. Each optionally substituted group is independently substituted by one or more halogen atoms or nitro, cyano, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, phenyl, mono- di- or trihalo-phenyl or pyridyl groups.

In general terms, unless otherwise stated, as used herein the term "halogen" may denote a bromine, iodine, chlorine or fluorine atom, and is preferably a bromine, chlorine or fluorine atom.

In general terms, unless otherwise stated herein, the terms "alkyl," "alkenyl," "alkanoyl," "acyl" and "alkoxy' as used herein with respect to a radical or moiety refer to a straight or branched chain radical or moiety. As a rule, such radicals have up to 10, in particular up to 6 carbon atoms. Suitably an alkyl or alkoxy moiety has from 1 to 6 carbon atoms, preferably from 1 to 5 carbon atoms. A preferred alkyl moiety is the methyl, ethyl, n-propyl, isopropyl or n-butyl group. A preferred acyl moiety is acetyl or propionyl.

The invention especially relates to compounds of the general formula I in which any alkyl part of the groups $R^1$ through $R^6$, which may be straight chained or branched, contains 1 to 10 carbon atoms, preferably 1 to 9 carbon atoms, more preferably 1 to 6 carbon atoms, and in which each optionally substituted group independently may be substituted by one or more halogen atoms or nitro, cyano, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, phenyl, or pyridyl groups, in which the phenyl moiety is optionally substituted by one to three substituents selected from halogen atoms, cyano, $C_{1-6}$alkyl and $C_{1-6}$ alkoxy groups.

The invention especially relates to compounds of the general formula I in which $R^1$ represents a straight-chained or branched $C_{1-10}$ alkoxyimino-$C_{2-10}$ alkyl, in particular a straight-chained 1-($C_{1-6}$ alkoxyimino)-$C_{2-6}$ alkyl group, in which the alkoxy moiety may be unsubstituted or substituted by 1 to 3 substituents selected from the group consisting of halogen atoms, aryl, alkyl, alkoxy, haloalkyl and haloalkoxy groups, most preferably being a 1-(methoxyimino)-ethyl, 1-(methoxyimino)-n-propyl, 1-(ethoxyimino)-ethyl group or a 1-(benzyloxyimino)-ethyl group.

The invention especially relates to compounds of the general formula I in which $R^2$ represents a $C_{1-10}$ alkoxy group, in particular a methoxy group.

The melithiazole derivatives of formula I are oils, gums, or, predominantly, crystalline solid materials and possess valuable fungicidal properties. Besides use as a fungicide for control of diseases in agronomic crops, the compound may be used as a biocide for the control of insect pests and nematodes, as a biocide of human/animal diseases/pests, and as a protectant or preservative for wood, leather or tissue. As fungicides in agronomic crops the compounds of the present invention can protectively and curatively be used against a broad spectrum of diseases in plant and fruit production such as grain producing crops (wheat, barley, rice, rye, triticale, oat, maize, sorghum and others), grape vine plants and fruits, solanaceous crops (potato, tomato, tobacco, pepper and others) top fruit, stone fruits, soft fruits and fruit crops (apples, pears, citrus, mango, bananas, coffee, cocoa and others), oil producing crops (soybeans, sunflowers, groundnuts, rape, olives, palms and others), vegetables (like beans, lettuce, cucumbers, pumpkins, brassicas and others), horticultural plants, hops, sugarbeets, ornamentals, flowers, forestry trees and crops and others. In all crops all parts of the plant can be protected by the compounds including roots, stems, leaves, flowers and fruits. A broad spectrum of diseases belonging to the Oomycetes, Ascomycetes, Basidiomycetes, Hymenomycetes and Fungi Imperfecti are controlled. Examples (but not excluding others) of such diseases are powdery mildews, downy mildews and late blights, anthracnoses, septorioses, blasts and blights, scabs and spots, blotches, rots on fruits, stems, leaves and roots, rusts, alternarioses, cercosporoses, sclerotinioses, moulds, wilts, smuts and bunts and others.

The melithiazole compounds of formula I possess a high fungicidal activity over a wide concentration range. Moreover, these compounds show enhanced curative and residual control of fungi and fungal diseases such as cereal, grape, apple and solanaceous crops diseases, and improved foliar systemicity compared with conventional fungicides.

Good results in terms of control of diseases caused by phythopathogenic fungi are obtained with melithiazole derivatives as defined in formula I, wherein
$R^1$ represents an optionally substituted alkyl, alkenyl, alkyloxiranyl, hydroxyalkyl, alkoxyalkyl, alkanoyloxyalkyl, hydroximinoalkyl, alkoxyiminoalkyl, hydrazonoalkyl or alkylhydrazonoalkyl group;
$R^2$ represents a methoxy group,
$R^3$ represents a methyl group,
$R^4$ represents a hydrogen atom.

In particular, the compounds of formula I are preferred, wherein:
a) $R^1$ represents an iminoalkyl group of formula

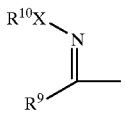

wherein
X represents O or $NR^{11}$; and
$R^9$, $R^{10}$ and $R^{11}$ each independently represent a hydrogen atom or an alkyl, aryl or heteroaryl group, preferably wherein $R^1$ represents a 1-($C_{1-3}$ alkoxyimino)-alkyl group, in particular 1-(methoxyimino)ethyl; or
b) $R^1$ represents an alkenyl group of formula

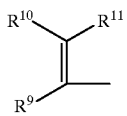

wherein
$R^9$ and $R^{10}$ each independently represent a hydrogen atom or an alkyl, aryl or heteroaryl group, and $R^{11}$ is a hydrogen atom or an alkyl, aryl, acyl or heteroaryl group, in particular wherein $R^9$ represents a $C_{1-6}$ alkyl group, one of $R^{10}$ and $R^{11}$ represents a hydrogen atom or a $C_{1-6}$ alkyl group and the other represents a hydrogen atom; or
c) $R^1$ represents a hydroxyalkyl group of formula

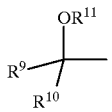

wherein
$R^9$ and $R^{10}$ each independently represent a hydrogen atom or an alkyl, aryl, or heteroaryl group, and $R^{11}$ is a hydrogen atom or an alkyl, aryl, acyl or heteroaryl group, in particular wherein $R^9$ represents a $C_{1-6}$ alkyl group, $R^{10}$ represents a hydrogen atom and $R^{11}$ represents a $C_{1-6}$alkyl or $C_{1-6}$ acyl group.

Especially good results in terms of control of phytopathogenic fungi are obtained by using melithiazole derivatives of formula IA

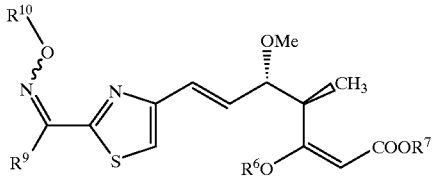

(IA)

and, for example, the melithiazole C methoxime (coded MCM) of formula

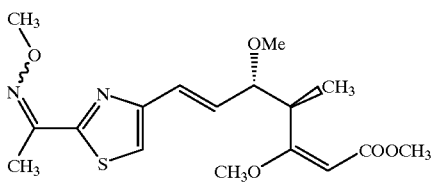

Generally, the present invention provides a process for preparing a melithiazole derivative of the general formula I

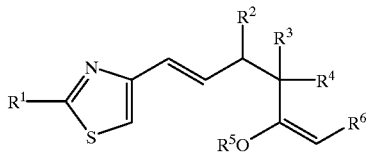
(I)

wherein
R$^1$ represents a hydrogen atom or an optionally substituted alkyl, alkenyl, alkyloxiranyl, alkanoyl, alkoxycarbonyl, formyl, hydroxyalkyl, alkoxyalkyl, alkanoyloxyalkyl, hydroximinoalkyl, alkoxyiminoalkyl, hydrazonoalkyl or alkylhydrazonoalkyl group;
R$^2$ represents an alkoxy group;
R$^3$ and R$^4$ each independently represent a hydrogen atom or an alkyl group;
R$^5$ represents an alkyl group, and
R$^6$ represents a group of formula —COOR$^7$ or —CONR$^7$R$^8$, in which R$^7$ and R$^8$ each independently represent a hydrogen atom or an alkyl group; with the proviso that melithiazole C or the corresponding amide thereof of formula,

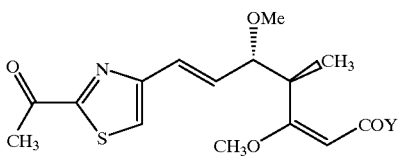

wherein Y represents NH$_2$ or OCH$_3$, are excluded which comprises one of the following:

i) reacting an amide of formula I wherein R$^6$ is CONR$^7$R$^8$ with a compound of formula II,

(R$^7$)$_3$OBF$_4$ (II)

in which R$^7$ is as hereinbefore defined to give a corresponding compound of formula I wherein R$^6$ is COOR$^7$; or ii) reacting a compound of formula I wherein R$^6$ is COOR$^7$ with an amine of formula III,

R$^7$R$^8$NH (III)

in which R$^7$ and R$^8$ are as hereinbefore defined, in the presence of an trialkylaluminium compound to give a corresponding compound of formula I wherein R$^6$ is —CONR$^7$R$^8$; or iii) reacting a compound of formula Va or epimer thereof

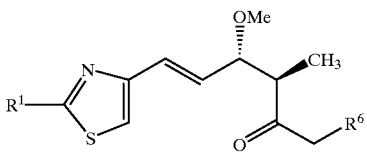
(Va)

wherein R$^1$ and R$^6$ are as hereinbefore defined, with an ortho-formate of formula VI,

HC(OR$^5$)$_3$ (VI)

in which R$^5$ is as hereinbefore defined, to give a compound of formula I where R$^5$ represents an alkyl group, or iv) reacting a compound of formula I, in which R$^1$ represents an acyl group with an amino derivative of formula VII,

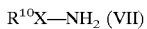
R$^{10}$X—NH$_2$ (VII)

in which R$^{10}$ is a hydrogen atom or an alkyl, aryl or heteroaryl group and X is O or NR$^{11}$ where R$^{11}$ is a hydrogen atom or an alkyl, aryl or heteroaryl group, to give a compound of formula I wherein R$^1$ represents an iminoalkyl group of formula

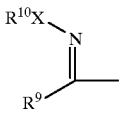

in which X, R$^9$ and R$^{10}$ are as defined above; or v) reacting a compound of formula I, in which R$^1$ represents an acyl group, with an ylid of formula VIII,

R$^{10}$R$^{11}$C=P(O)$_n$(R')$_3$ (VIII)

wherein R$^{10}$ and R$^{11}$ are as hereinbefore defined, and R' represents an alkyl or alkoxy group, and n is 0 or 1 to give a corresponding compound of formula I wherein R$^1$ represents an alkenyl group of formula

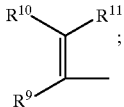

wherein R$^9$, R$^{10}$ and R$^{11}$ are as hereinbefore defined; or vi) reducing a compound of formula I wherein R$^1$ is formyl or alkanoyl with a reducing agent to give a compound of formula I wherein R$^1$ is hydroxyalkyl; or vii) acylating a compound of formula I wherein R$^1$ is hydroxyalkyl with an acylating agent containing an alkanoyl group to give a corresponding compound of formula I wherein R$^1$ is alkanoyloxyalkyl; or viii) reacting a compound of formula I wherein R$^1$ is hydroxyalkyl with an alkyl halide to give a corresponding compound of formula I wherein R$^1$ is alkoxyalkyl; or ix) reacting a compound of formula I wherein R$^1$ is alkanoyl with diazomethane to give a compound of formula I wherein R$^1$ is alkyloxiranyl;

The present invention provides a process for the preparation of a compound of formula I, wherein R$^1$ represents an acetyl group and R$^6$ represents a group of formula —COOR$^7$, in which R$^7$ represents an alkyl group other than methyl, which comprises treating the amide of melithiazole C with a compound of formula II, $$(R^7)_3OBF_4 \tag{II}$$

The present invention further provides a process for the preparation of a compound of formula I, wherein $R^1$ represents an acetyl group and $R^6$ represents a group of formula —$CONR^7RI$, in which $R^7$ represents an alkyl group and $R^8$ represents a hydrogen atom or an alkyl group, which comprises treating melithiazole C with an amine of formula III, $$R^7R^8NH \tag{III}$$

in the presence of a trialkylaluminium compound.

Furthermore, the compounds of formula I, wherein $R^1$ represents an acetyl group, can be prepared by a process which comprises the steps of:
(a) hydrolyzing a melithiazole derivative of formula IV,

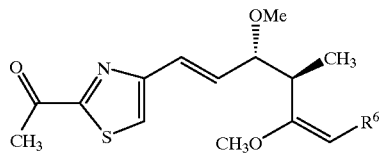
(IV)

(b) optionally epimerizing the resulting 3-oxo compound of formula V

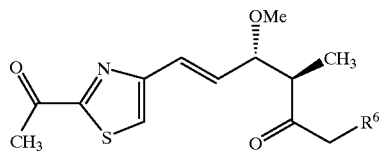
(V)

wherein $R^6$ is as hereinbefore defined, in the presence of a base; and
(c) treating compound of formula V with an ortho-formate of formula VI, $$HC(OR^5)_3 \tag{VI}$$

in which $R^5$ is as hereinbefore defined.

The present invention also provides a process for the preparation of a compound of formula I, wherein $R^1$ represents an iminoalkyl group of formula

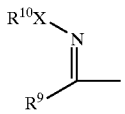

in which $R^9$, $R^{10}$ and X are as hereinbefore defined, which comprises reacting a compound of formula I, in which $R^1$ represents an acyl group of formula $R^9$—CO—, with an amino derivative of formula VII, $$R^{10}X—NH_2 \tag{VII}$$

in which $R^{10}$ and X are as hereinbefore defined.

Moreover, the present invention further provides a process for the preparation of a compound of formula I, wherein $R^1$ represents an alkenyl group of formula

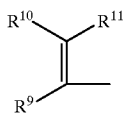

in which
$R^9$, $R^{10}$ and $R^{11}$ are as hereinbefore defined, which comprises reacting a compound of formula I, in which $R^1$ represents an acyl group of formula $R^9$—CO—, with an ylid of formula VIII, $$R^{10}R^{11}C=P(O)^n(R')_3 \tag{VIII}$$

wherein $R^{10}$ and $R^{11}$ are as hereinbefore defined, and R' represents an alkyl or alkoxy group, and n is 0 or 1.

The present invention further relates to compounds of formula V

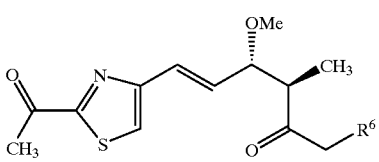
(V)

wherein $R^6$ is as hereinbefore defined.

Melithiazole C, the amide thereof and the compounds of formulae II, VII and VIII are known products, and may themselves be prepared according to established methods or routine adaptations thereof. Substituents which are not compatible with the selected reaction conditions may be introduced afterwards. They can be generated by known methods such as subsequent derivatization or substitution of a suitable group or by cleavage of a suitable protecting group.

The reaction between the amide of melithiazole C and the trialkoxonium tetrafluoroborate of formula If is preferably carried out analogously to known methods, e.g. Kiesling et al., *Synth. Commun.* 1997, 27, 923–937. As a rule it is carried out in the presence of an inert solvent, such as an optionally halogenated hydrocarbon like tetrachloromethane or dichloromethane, or an alcohol of formula $R^7$—OH or in mixtures of these solvents. The molar ratio between the amide and formula II is in the range of 0.3 to 1.9. The reaction is preferably carried out at a temperature between 0 and 150° C., in particular, at ambient temperature.

In this reaction, an alkyliminoester salt of formula

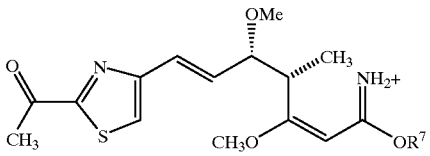

BF$_4$- is first formed and then subsequently hydrolysed to the desired ester.

In a preferred embodiment, the first step of this reaction is carried out with trimethoxonium tetrafluoroborate and the alcoholysis is carried out in the presence of an alcohol other than methanol. The alkyliminoester is preferably hydrolysed in a buffer system at a pH of 3 to 6, preferably 4 to 5, in particular at about pH 4.5.

The reaction between melithiazole C and the amine of formula III in the presence of trialkylaluminium is carried out analogously to known methods, e.g. A. Baska et al., *Tetrahedron Lett.* 1977, 4171–4173.

The compounds of formula IV are preferably hydrolysed using a carboxylic acid, in particular trifluoroacetic acid, with traces of water in an inert solvent such as optionally halogenated hydrocarbons like tetrachloromethane or dichloromethane.

The resulting 3-oxo-compounds are treated with an orthoester of formula VI analogously to known methods, e.g. W. J. Le Noble, *Synthesis* 1970, 1–6.

The processes described below can analogously be applied to other starting compounds, if desired.

Due to excellent fungicidal activity, the compounds of formula I can be used in cultivation of all plants where infection by phytopathogenic fungi is undesirable, e.g. cereals, solanaceous crops, vegetables, legumes, apples, vine.

The compounds of general formula I have been found to have fungicidal activity. Accordingly, the invention further provides a fungicidal composition which comprises, as an active ingredient, at least one compound of formula I, together with one or more carriers. A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A fungicidal composition according to the invention preferably contains from 0.5% to 95% by weight (w/w) of the active ingredient[s], together with a carrier therefor.

A carrier in the composition of the invention is any material with which the active ingredient is formulated to facilitate application to the locus to be treated, which may for example be a plant, seed, soil, or water in which a plant grows, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels, tablets and other formulation types by well-established procedures. These procedures include intensive mixing and/or milling of the active ingredients with other substances, such as fillers, solvents, solid carriers, surface active compounds (surfactants), and optionally, solid and/or liquid auxiliaries and/or adjuvants. The form of application such as spraying, atomizing, dispersing or pouring may be chosen, like the compositions according, to the desired objectives and the given circumstances.

Suitable solvents are those such as aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable as solvents.

Solid carriers, which can be used for dusts, wettable powders, water dispersible granules, or granules, can be mineral fillers, such as calcite, talc, kaolin, montmorillonite or attapulgite. The physical properties may be improved by addition of highly dispersed silica gel or polymers. Carriers for granules can be porous material, e.g. pumice, kaolin, sepiolite, bentonite; non-sorptive carriers can be calcite or sand. Additionally, a multitude of pre-granulated inorganic or organic materials can be used, such as dolomite or crushed plant residues.

Fungicidal pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also include mixtures of individual surfactants.

The fungicidal compositions of the invention may, for example, be formulated as wettable powders, water dispersible granules, dusts, granules, tablets, solutions, emulsifiable concentrates, emulsions, suspension concentrates and aerosols. Wettable powders usually contain 5 30 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% wow of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the fungicidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

| | Emulsion Concentrate (EC) | |
|---|---|---|
| Active Ingredient | MCM | 30% (w/v) |
| Emulsifier(s) | Atlox ® 4856 B/Atlox ® 4858 B[1] (mixture containing calcium alkyl aryl sulfonate, fatty alcohol ethoxylates and light aromatics/mixture containing calcium alkyl aryl sulfonate, fatty alcohol ethoxylates and light aromatics) | 5% (w/v) |
| Solvent | Shellsol ® A[2] (mixture of $C_9$–$C_{10}$ aromatic hydrocarbons) | to 1000 ml |
| | Suspension Concentrate (SC) | |
| Active Ingredient | MCM | 50% (w/v) |
| Dispersing agent | Soprophor ® FL[3] (polyoxyethylene polyaryl phenyl ether phosphate amine salt) | 3% (w/v) |
| Antifoaming agent | Rhodorsil ® 422[3] (nonionic aqueous emulsion of polydimethylsiloxanes) | 0.2% (w/v) |
| Structure agent | Kelzan ® S[4] (Xanthan gum) | 0.2% (w/v) |
| Antifreezing agent | Propylene glycol | 5% (w/v) |
| Biocidal agent | Proxel ®[5] (aqueous dipropylene glycol solution containing 20% 1,2-benisothiazolin-3-one) | 0.1% (w/v) |
| Water | | to 1000 ml |
| | Wettable Powder (WP) | |
| Active Ingredient | MCM | 60% (w/w) |
| Wetting agent | Atlox ® 4995[1] (polyoxyethylene alkyl ether) | 2% (w/w) |
| Dispersing agent | Witcosperse ® D-60[6] (mixture of sodium salts of condensed naphthalene sulfonic acid and alkylarylpolyoxy acetates) | 3% (w/w) |
| Carrier/Filler | Kaolin | 35% (w/w) |
| | Water Dispersible Granules (WG) | |
| Active Ingredient | MCM | 50% (w/w) |
| Dispersing/ Binding agent | Witcosperse ® D-450[6] (mixture of sodium salts of condensed naphthalene sulfonic acid and alkyl sulfonates) | 8% (w/w) |
| Wetting agent | Morwet ® EFW[6] (formaldehyde condensation product) | 2% (w/w) |
| Antifoaming agent | Rhodorsil ® EP 6703[3] (encapsulated silicone) | 1% (w/w) |
| Disintegrant | Agrimer ® ATF[7] (cross-linked homopolymer of N-vinyl-2-pyrrolidone) | 2% (w/w) |
| Carrier/Filler | Kaolin | 35% (w/w) |

[1] commercially available from ICI Surfactants
[2] commercially available from Deutsche Shell AG
[3] commercially available from Rhône-Poulenc
[4] commercially available from Kelco Co.
[5] commercially available from Zeneca
[6] commercially available from Witco
[7] commercially available from International Speciality Products The compositions of this invention can also comprise other compounds having biological activity, e.g. compounds having similar or complementary pesticidal activity or compounds having plant growth regulating, fungicidal or insecticidal activity. These mixtures of pesticides can have a broader spectrum of activity than the compound of general formula I alone. Furthermore, the other pesticide can have a synergistic effect on the pesticidal activity of the compound of general formula I.

The other fungicidal compound can be, for example, one which is also capable of combating diseases of cereals (e.g. wheat) such as those caused by Erysipha, Puccinia, Septoria, Gibberella and Helminthosporium spp., seed and soil borne diseases and downy and powdery mildews on vines, early and late blight on solanaceous crops, and powdery mildew and scab on apples etc. These mixtures of fungicides can have a broader spectrum of activity than the compound of general formula I alone. Furthermore, the other fungicide can have a synergistic effect on the fungicidal activities of the compound of general formula I.

Examples of the other fungicidal compounds utilizable in the compositions of the present invention are anilazine, azoxystrobin, benalaxyl, benomyl, bethoxazin, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenarimot, fenbuconazole, fenfuram, fenhexamid, fenpicionil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, imazalil, iminoctadine, ipconazole, iprodione, isoprothiolane, kasugamycin, kitazin P, kresoxim-methyl, mancozeb, maneb, mepanipyrim, mepronil, metalaxyl, metconazole, methfuroxam, myclobutanil, neoasozin, nickel dimethyidithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, triflumizole, triforine, triticonazole, validamycin A, vinclozolin, XRD-563, zarilamid, zineb, ziram.

In addition, the co-formulations according to the invention may contain at least one compound of formula I and any of the following classes of biological control agents such as viruses, bacteria, nematodes, fungi, and other microorganisms which are suitable to control insects, weeds or plant diseases or to induce host resistance in the plants. Examples of such biological control agents are: *Bacillus thuringiensis, Verticillium lecanii, Autographica califomica NPV, Beauvada bassiana, Ampelomyces quisqualis, Bacilis subtilis, Pseudomonas chiororaphis, Pseudomonas fluorescens, Steptomyces griseoviddis* and *Trichoderma harzianum*.

Moreover, the co-formulations according to the invention may contain at least one compound of formula I and a chemical agent that induces the systemic acquired resistance in plants such as, for example, nicotinic acid or derivatives thereof or BION.

The compounds of general formula I can be mixed with soil, peat or other rooting media for the protection of the plants against seed-borne, soil-borne or foliar fungal diseases.

The invention still further provides the use as a fungicide of a compound of the general formula I as defined above or a composition as defined above, and a method for combating fungus at a locus, which comprises treating the locus, which may be, for example, plants subject to or subjected to fungal attack, seeds of such plants or the medium in which such plants are growing or are to be grown, with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes, vegetables and tomatoes. The duration of the protection is normally dependent on the individual compound selected, and also a variety of external factors, such as climate, whose impact is normally mitigated by the use of a suitable formulation.

The compounds according to the invention have curative, protective and residual activity and are systemic in plants. The compounds control diseases after foliar, soil, into water or seed application. They can be applied in different formulations. The compounds have better curative and systemic properties than current commercialized strobilurine derivatives.

The following examples further illustrate the present invention. It should be understood, however, that the invention is not limited solely to the particular examples given below.

EXAMPLE 1

Preparation of melithiazole C-amide

[7-(2-acetylthiazol-4-yl)-3,5-dimethoxy-4-methylheptan-2,6-dienoic amide]

A solution of diisobutylaluminium hydride (DIBAH, 8.6 ml, 1 m solution) in n-hexane is added to a mixture of myxothiazol A (800 mg, technical quality, 1.15 mmol) and dichloromethane (15 ml) at −70° C. The mixture is stirred at −70° C. for one hour. The reaction mixture is poured into a saturated aqueous solution of ammonium chloride (10 ml) and allowed to warm-up to ambient temperature. The reaction mixture is concentrated and extracted with ether (3 times). The organic phase is separated, dried and concentrated in vacuo. The residue is purified by MPL chromatography (column: Eurosil Bioselect 100-20-C-18, 15–25 μm, 32×3 cm, eluent: methanol/water) yielding the pure product, 209 mg (56 %).

$R_f$ (dichloromethane/methanol 90/10): 0.50

$R_t$ (methanol/water 55/45): 4.7 min

| $^1$H-NMR (300 MHz, CDCl$_3$): | | |
|---|---|---|
| | $\delta_H$ [ppm] | J [Hz] |
| 2-H (s) | 4.93 | |
| 3-OCH$_3$ (s) | 3.57 | |
| 4-H (dq) | 4.14 | 7.0, 7.0 |
| 4-CH$_3$ (d) | 1.15 | 7.0 |
| 5-H (dd) | 3.81 | 7.0, 7.6 |
| 5-OCH$_3$ (s) | 3.32 | |
| 6-H (dd) | 6.45 | 7.6, 15.8 |
| 7-H (d) | 6.58 | 15.8 |
| 9-H (s) | 7.40 | |
| 12-H$_3$ (s) | 2.70 | |

| $^{13}$C-NMR (75.5 MHz, CDCl$_3$): | |
|---|---|
| | $\delta_C$ [ppm] |
| C-1 | 169.1 |
| C-2 | 94.1 |
| C-3 | 172.0 |
| 3-OCH$_3$ | 55.1 |
| C-5 | 39.5 |
| 4-CH$_3$ | 14.1 |
| C-5 | 84.9 |
| 5-OCH$_3$ | 56.9 |
| C-6 | 132.9 |
| C-7 | 125.0 |
| C-8 | 155.6 |
| C-9 | 121.5 |
| C-10 | 166.5 |
| C-11 | 191.9 |
| C-12 | 26.0 |

IR (KBr): ν=668 cm$^{-1}$ (m), 825 (w), 935 (m), 953 (m), 970 (m), 1017 (w), 1057 (m), 1093 (s), 1125 (m), 1186 (m), 1216 (s), 1274 (m), 1329 (m), 1259 (m), 1413 (m), 1441 (m), 1485 (m), 1599 (s), 1685 (s), 2823 (w), 2879 (w), 2935 (m), 2970 (m), 3101 (w), 3191 (m), 3342 (m), 3448 (m).

UV (m ethanol): $\lambda_{max}$(log ε)=232 nm (4.59), 325 (3.61).

DCI MS (120 eV, i-butane): 325 [M$^+$H$^+$], 293.—C$_{15}$H$_{21}$N$_2$O$_4$S: calculated 325.1222, found 325.1202 (MS).

EXAMPLE 2

Preparation of melithiazole C

[methyl 7-(2-acetylthiazol-4-yl)-3,5-dimethoxy-4-methylheptan-2,6-dienoate]

28 mg (189 mmol) of trimethyloxonium tetrafluoroborate are added to a mixture of 40 mg (123.5 mmol) of the compound of Example 1 and 1 ml of dichloromethane. The mixture is stirred for 2.5 hours at room temperature, the solvent is removed of in vacuo, and the residue is dissolved in 14 ml of methanol and 8 ml 1 M of an aqueous sodium acetate buffer (pH 4.5). Upon heating to 70–75° C. for 3 hours the mixture is cooled to room temperature and methanol is removed of in vacuo. The aqueous phase is extracted with ether four times, the organic phases are combined and dried with sodium sulfate. The solvent is removed of in vacuo and the residue is purified by HPLC (methanol/water 60/40). 23 mg (55%) of melithiazole C, having a melting point 106° C., (re-crystallized from ethanol) are obtained.

R$_f$ (petrol ethers/diethylether 50/50): 0.52

$^1$H-NMR (300 MHz, CDCl$_3$):

|  | δ$_H$ [ppm] | J [Hz] |
|---|---|---|
| 2-H (s) | 4.96 | |
| 3-OCH$_3$ (s) | 3.59 | |
| 4-H (dq) | 4.16 | 7.4, 6.9 |
| 4-CH$_3$ (d) | 1.20 | 6.9 |
| 5-H (dd) | 3.81 | 7.4, 7.4 |
| 5-OCH$_3$ (s) | 3.32 | |
| 6-H (dd) | 6.45 | 7.5, 15.8 |
| 7-H (d) | 6.57 | 15.8 |
| 9-H (s) | 7.37 | |
| 12-H$_3$ (s) | 2.70 | |

$^{13}$C-NMR (75.5 MHz, CDCl$_3$):

|  | δ$_C$ [ppm] |
|---|---|
| C-1 | 167.7 |
| 1-OCH$_3$ | 50.8 |
| C-2 | 91.1 |
| C-3 | 176.6 |
| 3-OCH$_3$ | 55.6 |
| C-4 | 39.8 |
| 4-CH$_3$ | 14.0 |
| C-5 | 84.2 |
| 5-OCH$_3$ | 57.2 |
| C-6 | 133.3 |
| C-7 | 124.7 |
| C-8 | 155.6 |
| C-9 | 121.4 |
| C-10 | 166.5 |
| C-11 | 191.9 |
| C-12 | 26.0 |

IR (KBr): ν804 cm$^{-1}$ (w), 826 (m), 927 (m), 953 (m), 972 (m), 1054 (m), 1094 (s), 1126 (s), 1147 (s), 1194 (m), 1273 (s), 1360 (m), 1383 (m), 1486 (m), 1624 (s), 1689 (s), 1710 (s), 2936 (s), 2975 (m)

UV (methanol): λ$_{max}$(log ε)=234 nm (4.47), 325 (3;51).

DCI MS (120 eV, i-butane): 340 [M$^+$H$^+$], 308.— C$_{16}$H$_{21}$NO$_5$S: calculated 339.11405, found 339.11342 (MS).

EXAMPLE 3

Preparation of melithiazole C-methylamide

[7-(2-acetylthiazol-4-yl)-3,5-dimethoxy-4-methylheptan-2,6-dienoic methylamide]

A mixture of trimethylaluminium and hexane (75 μl, 150 μmol) is added to a mixture of methylamine and dichloromethane (obtained by introduction of methylamine into 1 ml of dichloromethane within 1 minute) and stirred at room temperature for 20 minutes. A mixture of 15 mg (44.2 μmol) melithiazole C as obtained in Example 2 and 300 μl of dichloromethane is added to the reaction mixture. The mixture is stirred for 2 hours at room temperature and acidified with 0.1 M hydrochloric acid. The phases are separated and the organic phase is washed with a saturated sodium bicarbonate solution and dried with sodium sulfate. The solvent is removed of in vacuo and the residue is purified by PSC (dichloromethane/methano 9:1). 11 mg (74%) of the desired product are obtained.

$^1$H-NMR (300 MHz, CDCl$_3$):

| δH [ppm] | J [Hz] |
|---|---|
| 3.94 | |
| 4.90 | |
| 3.80 | 7.0, 8.0 |
| 2.81 | 5.1 |
| 6.08 | |

EXAMPLES 4–7

Using essentially the same procedures described hereinabove for Examples 2 and 3 employing standard derivatization techniques where appropriate, the following compounds are prepared and shown in Table I:

TABLE I

| Example | Y |
|---|---|
| 4 | OC$_2$H$_5$ |
| 5 | OC$_3$H$_7$ |
| 6 | N(CH$_3$)$_2$ |
| 7 | NHC$_2$H$_5$ |

EXAMPLE 8

Preparation of melithiazole C methoxime (coded MCM) [Methyl 7-[2-(1-(E/Z)-methoxyimino)-ethyl]thiazol-4-yl)-3,5-dimethoxy-4-methylheptan-2,6-dienoate]

7 μl (86.7 nmol) pyridine are added to a mixture of 9 mg (26.6 μmol) melithiazole C as obtained in Example 2, 3 mg (35.9 μmol) O-methylhydroxylamine hydrochloride and 1 ml of ethanol. The reaction mixture is stirred for 2 hours at room temperature. The solvent is removed of in vacuo and the residue acidified with 0.1 M hydrochloric acid and extracted with ether. The combined organic phases are washed with a saturated sodium bicarbonate solution and dried with sodium sulfate. The solvent is removed of in vacuo and 9.5 mg (97%) MCM are obtained being a mixture of 57% (Z)-MCM and 43% (E)-MCM according to the 1H-NMR-data. The isomers are separated by preparative HPLC (methanol/water 75:25).

(Z)-MCM Rf (petrol ethers/diethylether 50/50): 0.57
Rt (Methanol/Wasser 80/20): 3.6 min
(E)-MCM: Rf (petrol ethers/diethylether 50/50): 0.64
Rt (methanol/water 80/20): 3.9 min.

$^1$H-NMR (300 MHz, CDCl$_3$):

|  | (Z)-MCM | | (E)-MCM, | |
|---|---|---|---|---|
|  | δH [ppm] | J [Hz] | δH [ppm] | J [Hz] |
| N=C—CH$_3$ (s) | 2.44 | | 2.33 | |
| 1-OCH$_3$ (s) | 3.65 | | 3.65 | |
| NOCH$_3$ (s) | 4.08 | | 4.01 | |

-continued

|  | (Z)-MCM | | (E)-MCM | |
| --- | --- | --- | --- | --- |
| 2-H (s) | 4.95 | | 4.95 | |
| 3-OCH₃ (s) | 3.58 | | 3.58 | |
| 4-H (dq) | 4.17 | 6.9, 7.5 | 4.15 | 6.9, 7.5 |
| 4-CH₃ (d) | 1.20 | 6.9 | 1.20 | 6.9 |
| 5-H (dd) | 3.79 | 7.5, 7.7 | 3.78 | 7.5, 7.7 |
| 5-OCH₃ (s) | 3.32 | | 3.31 | |
| 6-H (dd) | 6.40 | 7.7, 15.8 | 6.37 | 7.7, 15.7 |
| 7-H (d) | 6.59 | 15.8 | 6.52 | 15.7 |
| 9-H (s) | 7.29 | | 7.00 | |

$^{13}$C-NMR (75.5 MHz, CDCl₃):

|  | (Z)-MCM δC [ppm] | (E)-MCM, δC [ppm] |
| --- | --- | --- |
| C-1 | 167.7 | 167.7 |
| 1-OCH₃ | 50.8 | 50.8 |
| C-2 | 91.2 | 91.2 |
| C-3 | 176.6 | 176.6 |
| 3-OCH₃ | 55.5 | 55.5 |
| C-4 | 39.8 | 39.8 |
| 4-CH₃ | 14.1 | 14.1 |
| C-12 | 18.8 | 11.9 |
| C-5 | 84.4 | 84.4 |
| 5-OCH₃ | 57.1 | 57.1 |
| NOCH₃ | 62.4 | 62.7 |
| C-6 | 132.1 | 131.7 |
| C-7 | 125.5 | 125.3 |
| C-11 | 148.1 | 164.6 |
| C-8 | 152.6 | 152.0a) |
| C-9 | 118.6 | 115.5 |
| C-10 | 154.8 | 153.8 |

IR (KBr): (E/Z)-MCM: ν=826 cm$^{-1}$ (w), 898 (w), 927 (w), 973 (w), 992 (w), 1049 (s), 1071 (s), 1094 (s), 1126 (m), 1194 (m), 1223 (w), 1263 (m), 1305 (w), 1383 (m), 1438 (m), 1456 (w), 1487 (w), 1625 (s), 1712 (s), 2879 (w), 2902 (w), 2938 (m), 2973 (w).

UV (methanol): (E/Z)-MCM: $\lambda_{max}$(log e)=239 nm (4.62), 313 (3.81)

DCI MS (120 eV, i-butane): (EIZ)-MCM: 369 [M$^+$H$^+$], 337.—C₁₇H₂₄N₂O₅S: calculated 368.1406, found 368.1386 (MS).

EXAMPLES 9–18

Using essentially the same procedures described hereinabove for Example 8 employing standard derivatization techniques where appropriate, the following compounds are prepared and shown in Table II:

TABLE II

| Example | Y | imino configuration | R10 | Rf (petrol ethers/diethyl ether 50/50) |
| --- | --- | --- | --- | --- |
| 9 | OCH₃ | (Z) | benzyl | 0.58 |
| 10 | OCH₃ | (E) | benzyl | 0.62 |
| 11 | OCH₃ | (Z) | ethyl | 0.67 |
| 12 | OCH₃ | (E) | ethyl | 0.73 |
| 13 | OC₂H₅ | (Z) | methyl | |
| 14 | OC₂H₅ | (E) | methyl | |
| 15 | OC₂H₅ | (Z) | benzyl | |
| 16 | OC₂H₅ | (E) | benzyl | |
| 17 | OC₂H₅ | (Z) | ethyl | |
| 18 | OC₂H₅ | (E) | ethyl | |

EXAMPLE 19

Preparation of Dihydro melithiazole C
[Methyl 7-[2-(1-hydroxyethyl)thiazol-4-yl]-3,5-dimethoxy-4-methylheptan-2,6-dienoate]

1 mg (26.3 mmol) of sodium boranate is added to a mixture of 8 mg (23.6 μmol) melithiazole C as obtained in example 2 and 500 μl methanol at room temperature. After the reaction (DC-control) is complete the solvent is removed of in vacuo. The residue is diluted with water and ethyl acetate and extracted twice with ethyl acetate. The combined organic phases are dried with sodium sulfate. The solvent is removed of in vacuo and the residue is purified by preparative HPLC (methanol/water 55/45). 7 mg (87%) of the desired product are obtained.

Rf (dichloromethane/methanol 95/5): 0.26

$^1$H-NMR (300 MHz, CDCl₃):

|  | δH [ppm] | J [Hz] |
| --- | --- | --- |
| 1-OCH₃ (s) | 3.65 | |
| 2-H (s) | 4.94 | |
| 3-OCH₃ (s) | 3.58 | |
| 4-H (dq) | 4.13 | 6.9, 7.7 |
| 4-CH₃ (d) | 1.19 | 6.9 |
| 5-H (dd) | 3.77 | 7.7, 7.7 |
| 5-OCH₃ (s) | 3.30 | |
| 6-H (dd) | 6.33 | 7.7, 15.8 |
| 7-H (d) | 6.50 | 15.8 |
| 9-H (s) | 7.01 | |
| 12-CH₃ (d) | 1.62 | 6.5 |
| 11-H (m) | 5.10 | |

$^{13}$C-NMR (75.5 MHz, CDCl₃):

|  | δC [ppm] |
| --- | --- |
| C-1 | 167.7 |
| 1-OCH₃ | 50.8 |
| C-2 | 91.1 |
| C-3 | 176.7 |
| 3-OCH₃ | 55.6 |
| C-4 | 39.9 |
| 4-CH₃ | 14.1 |
| C-5 | 84.3 |
| 5-OCH₃ | 57.0 |
| C-6 | 131.7 |
| C-7 | 125.3 |
| C-8 | 153.3 |
| C-9 | 114.4 |
| C-10 | 175.2 |
| C-11 | 68.2 |
| C-12 | 24.1 |

IR (KBr): ν=826 cm−1(m), 926 (m), 969 (m), 1012 (w), 1051 (m), 1093 (s), 1126 (s), 1148 (s), 1195 (s), 1224 (w), 1266 (m), 1307 (m), 1384 (m), 1440 (m), 1455 (m), 1624 (s), 1711 (s), 2937 (m), 2978 (m), 3420 (m, br).

UV (Methanol): $\lambda_{max}$(log ε)=223 nm (4.27), 241 (4.36)

DCI MS (120 eV, i-butane): 342 [M$^+$H$^+$], 310.— $C_{16}H_{23}NO_5S$: calculated 341.1297, found 341.1291 (MS).

EXAMPLE 20

Preparation of O-Acetyl-dihydro melithiazole C

[Methyl 7-[2-(1-acetoxyethyl)thiazol-4-yl]-3,5-dimethoxy-4-methylheptan-2,6-dienoate]

50 µl of pyridine are added to a mixture of 4 mg (11.7 µmol) dihydro melithiazole C as obtained in Example 19 and 200 µl of acetic anhydride. The mixture is stirred for 4 hours at room temperature and subsequently acidified with 2 ml of 0.1 M hydrochloric acid. The aqueous phase is extracted with ethyl acetate 3 times, the combined organic phases are washed with a saturated sodium bicarbonate solution and dried with sodium sulfate. The solvent is removed of in vacuo and the residue is purified with preparative HPLC (methanol/water 58/42). 4 mg (89%) of the desired product are obtained.

Rf (dichloromethane/methanol 95/5): 0.40

$^1$H-NMR (300 MHz, CDCl$_3$):

| | δH [ppm] | J [Hz] |
|---|---|---|
| 1-OCH$_3$ (s) | 3.65 | |
| 2-H (s) | 4.94 | |
| 3-OCH$_3$ (s) | 3.58 | |
| 4-H (dq) | 4.13 | 6.9, 7.7 |
| 4-CH$_3$ (d) | 1.19 | 6.9 |
| 5-H (dd) | 3.77 | 7.7, 7.7 |
| 5-OCH$_3$ (s) | 3.30 | |
| 6-H (dd) | 6.33 | 7.7, 15.8 |
| 7-H (d) | 6.50 | 15.8 |
| 9-H (s) | 7.01 | |
| 12-CH$_3$ (d) | 1.67 | 6.5 |
| OCOCH$_3$ (s) | 2.13 | |
| 11-H (q) | 6.12 | 6.5 |

$^{13}$C-NMR (75.5 MHz, CDCl$_3$):

| | δC [ppm] |
|---|---|
| C-1 | 167.7 |
| 1-OCH$_3$ | 50.8 |
| C-2 | 91.1 |
| C-3 | 176.7 |
| 3-OCH$_3$ | 55.6 |
| C-4 | 39.8 |
| 4-CH$_3$ | 14.1 |
| C-5 | 84.3 |
| 5-OCH$_3$ | 57.0 |
| C-6 | 131.8 |
| C-7 | 125.3 |
| C-8 | 153.7 |
| C-9 | 114.4 |
| C-10 | 170.0 |
| C-11 | 69.9 |
| C-12 | 20.9 |

IR (KBr): µ=746cm−1 (w), 826 (w), 848 (w), 927 (m), 971 (m), 1051 (m), 1080 (m), 1094 (s), 1127 (m), 1147 (s), 1231 (s), 1264 (m), 1373 (m), 1383 (m), 1441 (m), 1454 (m), 1507 (w), 1625 (s), 1711 (s), 1749 (s), 2879 (w), 2938 (w), 2984 (w).

UV (Methanol): $\lambda_{max}$(log ε)=212 nm (4.20), 240 (4.30).

DCI MS (120 eV, i-butane): 384 [M$^+$H$^+$], 352.— $C_{18}H_{26}NO_6S$: calculated 384.1481, found 384.1470 (MS).

EXAMPLE 21

Preparation of O-Methyl-dihydro melithiazole C

[Methyl 7-[2-(1-methoxyethyl)thiazol-4-yl]-3,5-dimethoxy-4-methylheptan-2,6-dienoate]

20 mg (86.3 µmol) of silver(I)-oxide and 20 ml (320.6 µmol) of methyliodide are added to a mixture of 5 mg (14.7 µmol) of dihydro melithiazole C as obtained in Example 19 and 500 ml of ether at room temperature. The mixture is stirred at room temperature for 20 hours and filtered through Celite. The solvent is removed of in vacuo and the residue is purified with preparative HPLC.

Rf (dichloromethane/methanol 95/5): 0.47

$^1$H-NMR (300 MHz, CDCl$_3$):

| | δH [ppm] | J [Hz] |
|---|---|---|
| 1-OCH$_3$ (s) | 3.65 | |
| 2-H (s) | 4.94 | |
| 3-OCH$_3$ (s) | 3.58 | |
| 4-H (dq) | 4.13 | 6.8, 7.7 |
| 4-CH$_3$ (d) | 1.19 | 6.8 |
| 5-H (dd) | 3.78 | 7.8, 7.8 |
| 5-OCH$_3$ (s) | 3.30 | |
| 6-H (dd) | 6.30 | 7.8, 15.8 |
| 7-H (d) | 6.52 | 15.8 |
| 9-H (s) | 7.04 | |

$^{13}$C-NMR (75.5 MHz, CDCl$_3$):

| | δC [ppm] |
|---|---|
| C-1 | 167.7 |
| 1-OCH$_3$ | 50.8 |
| C-2 | 91.1 |
| C-3 | 176.8 |
| 3-OCH$_3$ | 55.6 |
| C-4 | 39.9 |
| 4-CH$_3$ | 14.1 |
| C-5 | 84.4 |
| 5-OCH$_3$ | 57.0 |
| C-6 | 131.4 |
| C-7 | 125.6 |
| C-8 | 153.4 |
| C-9 | 114.5 |
| C-10 | 174.3 |
| C-11 | 77.0 |
| C-12 | 22.4 |

DCI MS (120 eV, i-butane): 356 [M$^+$H$^+$].—$C_{17}H_{25}NO_5S$: calculated 355.1453, found 355.1423 (MS).

EXAMPLES 22–28

Using essentially the same procedures described hereinabove for Examples 19–21 employing standard derivatization techniques where appropriate, the following compounds are prepared and shown in Table III:

TABLE III

[Structure: R¹¹—O—CH(CH₃)—thiazole—CH=CH—CH(OMe)—CH(CH₃)—C(OCH₃)=CH—COY]

| Example | Y | R¹¹ |
|---|---|---|
| 22 | OCH₃ | C₂H₅CO |
| 23 | OCH₃ | C₂H₅ |
| 24 | OC₂H₅ | CH₃CO |
| 25 | OC₂H₅ | CH₃CO |
| 26 | OC₂H₅ | C₂H₅CO |
| 27 | OC₂H₅ | C₂H₅ |
| 28 | OC₂H₅ | H |

EXAMPLE 29

Preparation of Vinylidene-dihydro melithiazole C

[Methyl 7-[2-isopropenylthiazol-4-yl]-3,5-dimethoxy-4-methylheptan-2,6-dienoate]

A ready-to-use mixture of 25 mg (60.0 μmol) methyltriphenylphosphonium bromide/sodium amide (commercially available from Fluka, Art. No. 69500) is diluted with 400 ml of tetrahydrofuran at room temperature with stirring. A mixture of 8 mg (23.6 μmol) of melithiazole C as obtained in Example 2 and 400 ml of tetrahydrofuran is added. The resulting reaction mixture is stirred for 1.5 hours. The solvent is removed of in vacuo and the residue is diluted with water and ether. The aqueous phase is extracted with ether twice. The combined organic phases are dried with sodium sulfate. The solvent is removed of in vacuo and the residue is purified with preparative HPLC (methanol/water 65135). 5 mg (63%) of the desired product are obtained.

| Rf (dichloromethane/methanol 95/5): 0.63 | | |
|---|---|---|
| $^1$H-NMR (300 MHz, CDCl₃) | | |
| | δH [ppm] | J [Hz] |
| 1-OCH₃ (s) | 3.65 | |
| 2-H (s) | 4.95 | |
| 3-OCH₃ (s) | 3.58 | |
| 4-H (dq) | 4.15 | 6.9, 7.8 |
| 4-CH₃ (d) | 1.19 | 6.9 |
| 5-H (dd) | 3.78 | 7.8, 7.8 |
| 5-OCH₃ (s) | 3.31 | |
| 6-H (dd) | 6.36 | 7.8, 15.7 |
| 7-H (d) | 6.52 | 15.7 |
| 9-H (s) | 6.97 | |
| 11-CH₃ (s) | 2.22 | |
| 12-HA (s) | 5.83 | |

| $^{13}$C-NMR (75.5 MHz, CDCl₃): | |
|---|---|
| | δC [ppm] |
| C-1 | 167.7 |
| 1-OCH₃ | 50.8 |
| C-2 | 91.2 |
| C-3 | 176.7 |
| 3-OCH₃ | 55.5 |
| C-4 | 39.9 |
| 4-CH₃ | 14.1 |
| C-5 | 84.4 |
| 5-OCH₃ | 57.0 |
| C-6 | 131.6 |

-continued

| Rf (dichloromethane/methanol 95/5): 0.63 | |
|---|---|
| C-7 | 125.7 |
| C-8 | 154.1 |
| C-9 | 114.1 |
| C-10 | 169.1 |
| C-11 | 138.3 |
| C-12 | 116.5 |

IR (KBr): μ=825 cm−1 (m), 926 (m), 970 (w), 1050 (m), 1094 (s), 1147 (s), 1194 (m), 1265 (m), 1383 (m), 1440 (m), 1454 (m), 1624 (s), 1711 (s), 2937 (m), 2980 (m).

UV (methanol): $\lambda_{max}$(log ε)=233 nm (4.57), 301 (3.67).

DCI MS (120 eV, i-butane): 338 [M⁺H⁺], 306.—C₁₇H₂₃NO₄S: calculated 337.1348, found 337.11348 (MS).

EXAMPLES 30–40

Using essentially the same procedures described hereinabove for Example 29 employing standard derivatization techniques where appropriate, the following compounds are prepared and shown in Table IV:

TABLE IV

[Structure: R¹¹—C(CH₃)=C(R¹⁰)—thiazole—CH=CH—CH(OMe)—CH(CH₃)—C(OCH₃)=CH—COY]

| Example | Y | R¹⁰ | R¹¹ |
|---|---|---|---|
| 30 | OCH₃ | H | CH₃ |
| 31 | OCH₃ | H | C₂H₅ |
| 32 | OCH₃ | CH₃ | CH₃ |
| 33 | OCH₃ | H | C₅H₁₁ |
| 34 | OC₂H₅ | H | H |
| 35 | OC₂H₅ | H | CH₃ |
| 36 | OC₂H₅ | H | C₂H₅ |
| 37 | OC₂H₅ | CH₃ | CH₃ |
| 38 | NH₂ | H | H |
| 39 | NHCH₃ | H | H |
| 40 | NH₂ | CH₃ | CH₃ |

EXAMPLE 41

Preparation of Epoxy melithiazole C

[Methyl 7-[2-(1,2-epoxy-1-methylethyl)thiazol-4-yl]-3,5-dimethoxy-4-methylheptan-2,6-dienoate]

A freshly prepared solution of diazomethane is added to a mixture of 5 mg (14.7 mol) melithiazole C as obtained in example 2 and ether at room temperature. The mixture is stirred for 1 hour at room temperature and the solvent is removed of in vacuo. The residue is diluted with ether and water and the aqueous phase is extracted with water twice. The combined organic phases are dried with sodium sulfate. The solvent is removed of in vacuo and the residue is purified by PSC (ether/petrol ether 50/50). 2 mg (39%) of the desired product are obtained.

| | δH [ppm] | J [Hz] |
|---|---|---|
| | Rf (petrol ether/ether 50/50): 0.46 | |
| | ¹H-NMR (300 MHz, CDCl₃): | |
| 1-OCH₃ (s) | 3.65 | |
| 2-H (s) | 4.95 | |
| 3-OCH₃ (s) | 3.58 | |
| 4-H (m) | 4.13 | |
| 4-CH₃ (d) | 1.19 | 7.0 |
| 5-H (dd) | 3.77 | 7.6, 7.7 |
| 5-OCH₃ (s) | 3.31 | |
| 6-H (dd) | 6.34, 6.35 | 7.6, 15.7 |
| 7-H (d) | 6.49, 6.50 | 15.7 |
| 9-H (s) | 6.98 | |
| 11-CH₃ (s) | 1.84 | |
| 12-HA (d) | 3.04 | 5.4 |
| 12-HB (d) | 3.06 | 5.4 |

DCI MS (120 eV, i-butane): 354 [M⁺H⁺], 338, 322, 306.—$C_{17}H_{24}NO_5S$: calculated 354.1375, found 354.1359 (MS).

EXAMPLE 42

Preparation of Desmethyl melithiazole C

[Methyl 7-(2-acetylthiazol-4-yl]-5-methoxy-4-methyl-3-oxoheptan-6-enoate]

A mixture of 100 mg (295 μmol) melithiazole C as obtained in Example 2, 2 ml of dichloromethane and 200 μl of trifluoroacetic acid is kept at room temperature for 10 minutes. A saturated sodium bicarbonate solution is added and the solvent is distilled of in vacuo. The aqueous phase is extracted with water three times. The combined organic phases are dried with sodium sulfate. The solvent is removed of in vacuo to yield 94 mg (98%) of the desired product.

| | δH [ppm] | J [Hz] |
|---|---|---|
| | ¹H-NMR (300 MHz, CDCl₃) (selected signals): | |
| 1-OCH₃ (s) | 3.69 | |
| 2-H₂ | 3.54 | |
| 4-H (dd) | 2.97 | 5.0, 7.0 |
| 4-H (d) | 1.17 | 7.0 |

Biological Investigation (A) In-vitro

Determination of Minimum Inhibitory Concentration by Test Compounds in the Serial Dilution Test with *Botrytis cinera* (BOC), and *Hansenula anomala* (HNA).

The MIC (Minimum Inhibitory Concentration) value, which indicates the lowest concentration of the active ingredient in the growth medium which causes a total inhibition of mycelial growth, is determined by serial dilution tests. The compounds of the invention have been compared with known melithiazole C. melithiazole C-amide and with the commercially available strobilurines kresoxim-methyl (BASF AG) and azoxystrobin (ZENECA).

In addition, the toxicity $IC_{50}$ of these compounds has been evaluated using mouse fibroblasts (cell line L929). The therapeutic index given is defined as the ratio between the toxicity and the BOC-MIC value ($IC_{50}$/MIC). The results of these tests are shown in table V Table V

| Example | IC₅₀ [ng/ml] | MIC [ng/ml] (BOC) | MIC [ng/ml] (HNA) | Therapeutic Index |
|---|---|---|---|---|
| 8:(Z)-MCM | 500 | 5 | 80 | 100 |
| 8:(E)-MCM | 400 | 2.5 | 80 | 160 |
| 9 | 500 | 150 | 600 | 3.33 |
| 10 | 50 | 40 | 300 | 1.25 |
| (E/Z)-(13/14) | 200 | 5 | 20 | 40 |
| 20 | >4000 | 300 | 1250 | >13.33 |
| 21 | 2000 | 150 | 80 | 13.33 |
| 29 | 2000 | 20 | 300 | 100 |
| 41 | >3700 | 600 | 5000 | >6.17 |
| 1:melithiazole C-amide | 8000 | >10000 | >10000 | <0.8 |
| 2:melithiazole C | 550 | 1500 | 3000 | 0.37 |
| kresoxim-methyl | 375 | 100 | n.t. | 3.75 | n.t. denotes not tested (B) In-vivo

Test Procedure

Test Plants: Test plants were grown up in the greenhouse. Either seed, pregerminated seed or rooted vegetative plant material was planted in pots containing a fertilized soil/peat mixture. Test plants were used for treating them with the various fungicides when they were in the 3–4 leaf stage. The number of leaves of vegetatively propagated plant material was cut back to 3–4 leaves per plant.

Application: Test plants were treated with fungicides either 1 or 3 days before (protective treatments) or 2 or 3 days after (curative treatments) the inoculation with a pathogen. The test compounds were applied to the test plants using a lateral-nozzle sprayer with a turntable rotating the pots, or the test compounds were applied with an hand-held airbrush. 24 plants were used per treatment.

Compounds: Technical material of the compound according to the invention coded MCM, and of commercially available strobilurines kresoxim-methyl (BASF) and azoxystrobin (ZENECA) was dissolved in acetone with 0.5% Triton X155 at a concentration of 0.5%. For application to the test plants, the dissolved materials were further diluted with demineralized water to obtain final concentrations of 200, 50, 12.5, 3.1, 0.8 and 0.2 ppm ingredient. In other tests, concentrations of 20 and 4 ppm were used. The test plants were sprayed and wetted 'just before run-off' with the spray wash containing the desired compound concentration.

Inoculations and culture conditions: For the protective tests, treated plants were kept 1 or 3 days in the greenhouse and then inoculated with a pathogen. For inoculation an aqueous spore suspension was sprayed or spores were dusted onto the plants. Then the plants were kept in specific chambers for incubation if required, and then were moved to a greenhouse for disease development. For curative tests, plants were inoculated and, if required, incubated 2 or 3 days before the application of the compound, and then moved to a greenhouse after application of the compounds. The temperature in the greenhouse was between 18 and 25 degree C. The relative humidity was about 50–80% in the greenhouses and up to 100% in the incubation chambers. The plants were watered as required for good plant growth. In the greenhouse additional light was supplied to maintain a 14 hours day and 10 hours night cycle.

Assessment of diseases: The percentage of leaf area infected was assessed by visual estimation when untreated control plants were just completely diseased. Each plant was individually evaluated and then the mean infection rating was calculated for each treatment. The fungicidal activity was calculated using the following formula:

$$\% \text{ activity} = 100 - \frac{\text{infection in treated leaves}}{\text{infection in untreated leaves}} \times 100\%$$

The % activity is given in the results (examples) or from the % activity at each dose rate an effective dose for 90% disease control (ED90) was calculated. The lower the ED90 value (calculated is the ppm concentration in the spray wash required to control 90 % of the disease) of a compound for the control of a specific disease the higher the activity of that compound. The results a re shown in Tables VI to VIII.

Foliar systemicity: When the primary leaves of wheat planted in 8 cm diameter pots in the greenhouse were fully expanded, the plants were cut back to four leaves in each pot of which two were marked with a permanent marker 5 cm below the leaf tip on the upper leaf surface. Thus there were two band-treated and two untreated plants in each pot. A pipette was used to apply 5 ml of solution containing 400 ppm of the test compound (previously dissolved as described above) in a band on the lower leaf surface opposite the mark. The application band covered the whole leaf width. After application and after the bands were dried, the plants were moved to the greenhouse and kept there for 2 days to allow for movement of the compounds. The plants were kept by bottom watering. The plants were then inoculated by dusting them with powdery mildew conidia (*Erysiphe graminis*). Evaluations were made 7–8 days after inoculation. Distal and proximal movement were assessed as follows: The distal and proximal disease free zones on the upper leaf surface were measured in mm. The distal direction is from the band toward the leaf apex and the proximal direction is from the band towards the leaf base. The results of this evaluation are shown in Table IX:

Table VI: Examples of curative activity of MCM expressed as ED., values (ppm a.i.) for the control of barley powdery mildew (BPM—*Erysiphe graminis* on barley), grape vines powdery mildew (GPM—*Uncinula necator* on grape) and apple scab (AS—*Venturia inaequalis* on apple):

| Disease/Treatment | MCM | Kresoxim-methyl | Azoxystrobin |
|---|---|---|---|
| BPM | 0.4 ppm | 6.9 ppm | 5.9 ppm |
| GPM | 2.4 ppm | 39.4 ppm | 126 ppm |
| AS | 5.3 ppm | 34.1 ppm | 48.4 ppm |

Table VII: Examples of 3 day protective activity of MCM expressed as ED$_{90}$ values (ppm a.i.) against wheat septoriosis (WSN—*Lepthosphaeria nodorum*), wheat powdery mildew (WPM—*Erysiphe graminis*), wheat rust (WLR—*Puccinia recondita*), apple powdery mildew (APM—*Podosphaera leucotricha*), bean rust (BR—*Uromyces appendiculata* on phaseolus beans)

| Disease/Treatment | MCM | Kresoxim-methyl | Azoxystrobin |
|---|---|---|---|
| WSN | 34.0 ppm | 98.8 ppm | 24.9 ppm |
| WPM | 7.0 ppm | 1.9 ppm | 6.4 ppm |
| WLR | 12.0 ppm | 36.4 ppm | <0.2 ppm |
| APM | 2.7 ppm | 12.5 ppm | 1.7 ppm |
| BR | 102.0 ppm | 18.2 ppm | 0.05 ppm |

Table VIII: Curative (2 d cur) and protective (1 d res) activity (%) of MCM against grape downy mildew (GDM—*Plasmopara viticola*), tomato late blight (TLB—*Phytophthora infestans*) and barley net blotch (BNB—*Pyrenophora teres*)

| | MCM Dose (ppm) | | Kresoxim-methyl Dose (ppm) | |
|---|---|---|---|---|
| Disease/Treatment | 20 | 4 | 20 | 4 |
| GDM 2d cur | 59 | 0 | 9 | 0 |
| GDM 1 d res | 100 | 92 | 87 | 39 |
| TLB 1 d res | 65 | 25 | | |
| BNB 1 d res | 100 | 100 | 98 | 97 |

Table IX: Systemicity of MCM in wheat leaves (in mm) after foliar application using wheat powdery mildew as the indicator disease:

| Direction/Treatment | MCM | Kresoxim-methyl | Azoxystrobin |
|---|---|---|---|
| proximal | 21 | 13 | 9 |
| distal | 50 | 23 | 43 |

The results show that the curative activity and the foliar systemicity of the compound according to this invention coded MCM is better than that of the commercialized strobilurine derivatives kresoxim-methyl and azoxystrobin. In particular, the foliar systemicity and also the curative values imply that MCM had to penetrate the plant tissue to be active, and that, therefore, the compound is readily and highly bioavailable.

What is claimed is:
1. A melithiazole derivative of the general formula I

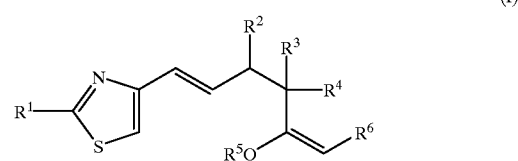

(I)

wherein

R$^1$ represents a hydrogen atom or an alkyl, alkenyl, alkyloxiranyl, alkanoyl, alkoxycarbonyl, formyl, hydroxyalkyl, alkoxyalkyl, alkanoyloxyalkyl, hydroximinoalkyl, alkoxyiminoalkyl, hydrazonoalkyl or alkylhydrazonoalkyl group;

R$^2$ represents an alkoxy group;

R$^3$ and R$^4$ each independently represent a hydrogen atom or an alkyl group;

R$^5$ represents an alkyl group, and

R$^6$ represents a group of formula —COOR$^7$ or —CONR$^7$R$^8$, in which R$^7$ and R$^8$ each independently represent a hydrogen atom or an alkyl group;

in which any alkyl part of the groups R$^1$ through R$^6$ contains 1 to 10 carbon atoms, with the proviso that melithiazole C or the corresponding amide thereof of formula,

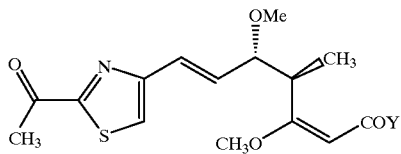

wherein Y represents $NH_2$ or $OCH_3$, are excluded.

2. A melithiazole derivative of the general formula I according to claim 1, in which $R^1$ represents an alkyl, alkenyl, alkyloxiranyl, hydroxyalkyl, alkoxyalkyl, hydroximinoalkyl, alkoxyiminoalkyl, hydrazonoalkyl or alkylhydrazonoalkyl group;

$R^2$ represents a methoxy group, $R^3$ represents a methyl group, $R^4$ represents a hydrogen atom.

3. A melithiazole derivative of the general formula I according to claim 1 or 2, in which $R^1$ represents an iminoalkyl group of formula

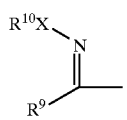

wherein

X represents O or $NR^{11}$; and $R^9$, $R^{10}$ and $R^{11}$ each independently represent a hydrogen atom or an alkyl group.

4. A compound as claimed in claim 3 wherein $R^1$ represents a 1-(methoxyimino)-alkyl group.

5. A melithiazole derivative of the general formula I according to claim 1 or 2, in which $R^1$ represents an alkenyl group of formula

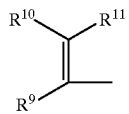

wherein $R^9$, $R^{10}$ and $R^{11}$ each independently represent a hydrogen atom or an alkyl group.

6. A melithiazole derivative of the general formula I according to claim 1 or 2, in which $R^1$ represents a hydroxyalkyl group of formula

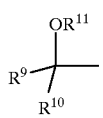

wherein $R^9$, $R^{10}$ and $R^{11}$ each independently represent a hydrogen atom or an alkyl group.

7. A melithiazole derivative according to claim 1 of formula

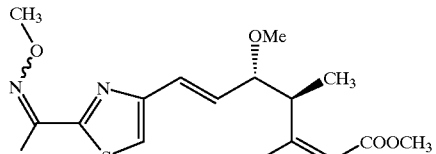

8. A process for the preparation of a compound of formula I as claimed in claim 1 which comprises one of the following (i) reacting an amide of formula I wherein $R^6$ is $CONR^7R^8$ with a compound of formula II,

in which $R^7$ is as hereinbefore defined to give a corresponding compound of formula I wherein $R^6$ is $COOR^7$; or (ii) reacting a compound of formula I, wherein $R^6$ is $COOR^7$ with an amine of formula III,

in which $R^7$ and $R^8$ are as hereinbefore defined, in the presence of an trialkylaluminim compound to give a corresponding compound of formula I wherein $R^6$ is $CONR^7R^8$; or (iii) reacting a compound of formula Va or epimer thereof

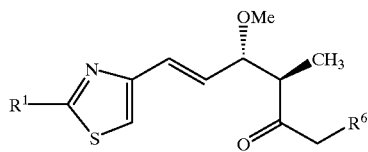

wherein $R^1$ and $R^6$ are as defined hereinabove, with an ortho-formate of formula VI,

in which $R^5$ is as hereinbefore defined, to give a compound of formula I where $R^5$ represents an alkyl group; or (iv) reacting a compound of formula I, in which $R^1$ represents an acyl group with an amino derivative of formula VII,

in which $R^{10}$ is a hydrogen atom or an alkyl group and X is O or $NR^{11}$ where $R^{11}$ is a hydrogen atom or an alkyl group, to give a compound of formula I, wherein $R^1$ represents an iminoalkyl group of formula

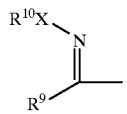

in which X, $R^9$ and $R^{10}$ are as defined above. or (v) reacting a compound of formula I, in which $R^1$ represents an acyl group with an ylid of formula VIII,

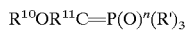   VIII wherein $R^{10}$ and $R^{11}$ are as hereinbefore defined, and R' represents an alkyl or alkoxy group, and n is 0 or 1 to give a corresponding compound of formula I, wherein $R^1$ represents an alkenyl group of formula

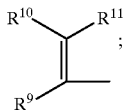

or (vi) reducing acompound of formula I wherein $R^1$ is formyl or alkanoyl with a reducing agent to give a compound of formula I wherein $R^1$ is hydroxyalkyl; or (vii) acylating a compound of formula I wherein $R^1$ is hyroxyalkyl with an acylating agent containing an alkanoyl group to give a corresponding compound of formula I wherein $R^1$ is alkanoyloxyalkyl; or (viii) reacting a compound of formula I wherein $R^1$ is hydroxyalkyl with an alkyl halide group to give a corresponding compound of formula I wherein $R^1$ is alkoxyalkyl; or (ix) reacting a compound of formula I wherein $R^1$ is alkanoyl with diazomethane to give a compound of formula I wherein $R^1$ is alkyloxiranyl.

9. A compound of formula V

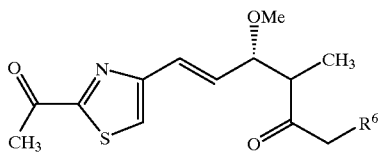

in which $R^6$ represents a group of formula —$COOR^7$ or —$CONR^7R^8$, in which $R^7$ and $R^8$ each independently represent a hydrogen atom or an alkyl group.

10. A fungicidal composition which comprises, as active agent, at least one compound of formula I as defined in claim 1 together with an agronomically acceptable carrier.

11. A method of combating fungi or fungal plant diseases at a locus such as a plant which comprises treating the locus with a compound of formula I as defined in claim 1 or with a composition as defined in claim 10.

12. The method according to claim 11 wherein the disease is caused by a phytopathogenic fungus selected from the group comprising Oomycetes, Ascomycetes, Basidiomycetes and Fungi imperfecti.

13. The method according to the claim 11 wherein the disease is controlled by the compound of formula I due to its high bioavailablity.

14. A process for preparing a fungicidal composition which comprises bringing at least one compound of formula I as defined in claim 1 into association with an agronomically acceptable carrier.

15. The composition according to claim 10 wherein the compound of formula I is melithiazole C methoxime.

16. The method according to claim 11 wherein the compound of formula I is melithiazole C methoxime.

* * * * *